(12) United States Patent
Hammond et al.

(10) Patent No.: US 6,750,025 B1
(45) Date of Patent: Jun. 15, 2004

(54) METHOD OF DETECTING AND ISOLATING PRION PROTEIN AND VARIANTS THEREOF

(75) Inventors: David J. Hammond, Cortlandt Manor; Emma L. Medina, Elmhurst, both of NY (US)

(73) Assignee: V.I. Technologies, Inc., Watertown, MA (US)

( * ) Notice: Subject to any disclaimer, the term of this patent is extended or adjusted under 35 U.S.C. 154(b) by 0 days.

(21) Appl. No.: 09/112,956

(22) Filed: Jul. 9, 1998

(51) Int. Cl.[7] .................. A61K 35/14; C07K 1/00; C12Q 1/00; G01N 33/53
(52) U.S. Cl. ............... 435/7.1; 435/4; 530/350; 530/380
(58) Field of Search ............ 435/7.1, 4; 530/350, 530/380

(56) References Cited

PUBLICATIONS

Calbiochem Biochemical and Immunochemical 1996/97 Catalog, pp. 327 and 441.*
Keulen et al. Immunohistochemical detection of prion prote in lymphoid tissues of sheep with natural scrapie. Journal of Clinical Microbiology. May 1996, vol. 34, No. 5, pp. 1228–1231, entire document.
Schmerr et al. Improvements in a competition assay to detect scrapie prion protein by capillary electrophoresis. Journal of Chromatography B. 1996, vol. 681, pp. 29–35, entire document.
Schmerr et al. Use of capillary sodium dodecyl sulfate gel electrophoresis to detect the prion protein extracted from scrapie-infected sheep. Journal of Chromatography B. 1997, vol. 697, pp. 223–229, entire document.

* cited by examiner

*Primary Examiner*—Deborah J. R. Clark
*Assistant Examiner*—Anne-Marie Baker
(74) *Attorney, Agent, or Firm*—Amster, Rothstein & Ebenstein

(57) ABSTRACT

The present invention provides for a novel method of detecting the prion protein and variants thereof which utilizes specific amino acid binding sequences. Specifically, the present invention provides a method of detecting prion proteins, as well as isolating prion proteins, using an agent that binds to the amino acid sequence Gln-Pro-His of prion proteins. Further provided by the present invention is a method of diagnosing prion diseases in a subject using an agent that binds to the amino acid sequence Gln-Pro-His of prion proteins. Also provided are methods of treating and preventing prion diseases in a subject by administering an agent that binds to the amino acid sequence Gln-Pro-His of prion proteins. Finally, a method of inhibiting the dissemination of prion diseases through ingestion or exposure to liquid or solid substances by treating of the liquid or solid substance with biotin is provided herein.

12 Claims, 6 Drawing Sheets

METHOD OF DETECTING AND ISOLATING PRION PROTEIN AND VARIANTS THEREOF

BACKGROUND OF THE INVENTION

Native prion protein ($PrP^c$) is widely distributed throughout nature and is particularly well conserved within mammals (Caughey and Chesebro, *Trends Cell Biol.* 7:56–62 (1997)). In man it is transcribed from a gene present on chromosome 20 (Sparks, et al. *Proc. Natl. Acad. Sci. USA* 83:7358–7362 (1986)). It is the conversion of the native $PrP^c$ protein to the infectious $PrP^{sc}$ protein which leads to the propagation of diseases such as kuru and Creutzfeld-Jakob disease in man, scrapie in sheep, bovine spongiform encephalopathy, transmissible mink encephalopathy, and wasting disease in deer and elk. The $PrP^c$ gene contains one open reading frame with end terminal sequencing of the expressed protein beginning early (position 3) in the open reading frame. In scrapie infected hamsters, the first amino acid of $PrP^c$ is lysine at position 3, and for the infectious $PrP^{sc}$ protein it is lysine at position 15 (Turk, et al. *Eur. J. Biochem.* 176:21–30 (1988)). In its natural form, the protein has a significant portion of random loop structure at the amino terminal which includes the octapeptide repeat sequences of Gly-Tyr-Gly-Gln-Pro-His-Gly-Gly (SEQ. ID NO: 1) (Miura, et al. FEBS Lett. 396:248–252 (1996)). Four repeats of this sequence are present between residues 53 and 91 of the open reading frame in the human protein. Some species, such as cattle, may have more repeats of this sequence. The protein in amyloid fibrils sometimes designated PrP 27–30 may lack this sequence while it is also removed experimentally through the action of proteinase K. The octapeptide sequence is highly conserved among mammalian prion proteins implying some structural and functional roles of the octapeptide. Being rich in glycine and praline neither alpha helix nor beta sheet are predicted for this region though it is able to assume structure in the presence of copper (Miura, et al. FEBS Lett. 396:248–252 (1996)). Prion protein is able to form a single intramolecular disulphide found between Cys 179 and 214. The translated protein is modified by glycosylation at two sites. In the hamster protein they are at positions 183 and 197 (Rogers, et al. Glycobiol. 1:101–109 (1990)). The expressed protein is localized to the outer surface of cell membranes by a glycoinositol phospholipid linked through ethanolamine attached to serine at position 231. It is a conformationally altered form of $PrP^c$ that is believed to be responsible for prion diseases. It is postulated that $PrP^c$ is converted into the infectious $PrP^{sc}$ protein through a posttranslational process during which it acquires a high β-sheet content (K. M. Pan, et al. *PNAS U.S.A.* 90:10962 (1993)). Sheet modification is believed to start at residues close to the carboxy terminal side of amino acid 100. It is thought likely that a non-infectious protein must interact directly with an infectious prion protein for this conversion to take place, and it has been proposed that sites exist on the central portion of the PrP molecule that allow specific binding between $PrP^c$ and $PrP^{sc}$ as a first step in the conversion of $PrP^c$ to $PrP^{sc}$ (Chabry, et al. 1998). It is not known how prion proteins interact together though it is considered likely that an additional protein or "chaperone" is required. This structural change of the factor is accompanied by changes in the properties of the protein. $PrP^{sc}$ protein is not soluble in nondenaturing agents, whereas $PrP^c$ is (R. K. Meyer, et al., *PNAS U.S.A.* 83:2310 (1986)); and $PrP^{sc}$ protein is partially resistant to digestion by proteases, whereas $PrP^c$ is highly digestable (B. Oesch, et al., *Cell* 40:735 (1985)).

Detection of prion protein is usually accomplished by the use of monoclonal antibodies, of which 3F4 is currently used extensively (Kascsak, et al. 1987). Antibody 3F4 recognizes the peptide sequence Met-Lys-His-Met (SEQ ID NO: 4) of the native conformation of $PrP^c$ and also Met-Lys-His-Met (SEQ ID NO: 4) of denatured, but not fibrils of $PrP^{sc}$. Consequently, in order to detect the presence of aggregates of $PrP^{sc}$, the proteins must first be denatured. A monoclonal specific for the resistant form has been reported, but its utility has not been verified. Other monoclonal antibodies have been reported, but in general their specificity and affinity for the prion protein are poor. The major problem in generating a sufficient immunological response to provide useful antibodies is the fact that the structure of prion proteins is highly conserved in animals, so immunogens comprising prions from different species are recognized by the immunized animal as host proteins. The amino terminal including the Gly-Tyr-Gly-Gln-Pro-His-Gly-Gly (SEQ ID NO: 1) repeat sequence of the protein is present as a random coil and presumably lacks a defined structure. Consequently, it will not be presented as a defined epitope.

Thus, a great need remains for a method of detection of $PrP^{sc}$ protein in a sample which overcomes the problems of the prior art methods, such as the methods using antibodies. Specifically, a method is needed that allows for the direct detection of $PrP^{sc}$ protein in a sample which is specific and does not require manipulation of the protein before detection. A method of detection of the $PrP^{sc}$ protein which overcomes the problems of the prior art will be extremely valuable for detecting and diagnosing prion diseases in a subject.

Finally, a need also remains for a way to bind prion proteins to each other to study their interaction. This would be an extremely valuable research tool for designing molecules that will interfere with the binding of prion proteins together and thus prevent the conversion of a native prion protein to one that is infectious.

SUMMARY OF THE INVENTION

The present invention provides a method of detecting prion protein in a sample. Using the method provided herein, all variants and strains of prion protein can be detected. The method comprises contacting the sample with an agent that binds to the amino acid sequence Gln-Pro-His of prion protein and detecting the agent bound to the prion protein. In order to detect the agent, the agent may be bound to a detectable marker, such as a radiolabel or an enzyme. In a specific embodiment of the invention, the agent is streptavidin which binds tightly and specifically to the Gln-Pro-His sequences of prion proteins.

The method of detection of prion proteins provided by the present invention overcomes the problems presented by the prior art methods of detection using antibodies. The method provided herein does not require denaturation of the prion proteins in order to detect them. Furthermore, unlike antibodies to a protein which vary in specificity from strain to strain, and most certainly from species to species, the novel method provided herein utilizes a highly conserved amino acid sequence of the prion protein as a binding site for agents such as streptavidin to bind to and allow for detection. The amino acid sequence utilized by the present invention is found to be highly conserved throughout all prion protein variants and strains, as well as throughout all species.

Also provided by the present invention is a method of isolating prion protein in a sample by contacting the sample with an agent that binds to the amino acid sequence Gln-Pro-His of prion protein and isolating the agent bound to the prion protein.

A method of diagnosing a prion disease in a subject is also provided by the present invention. This method comprises contacting a biological sample taken from the subject with an agent that binds to the Gln-Pro-His sequence of prion protein, then detecting the agent in the sample. The prion diseases which may be diagnosed using the method of the present invention are Creutzfeld-Jakob disease, Gerstmann-Sträussler-Scheinker disease, fatal familial insomnia, scrapie, bovine spongiform encephalopathy (mad cow disease), transmissible mink encephalopathy, feline spongiform encephalopathy, exotic ungulate encephalopathy, and chronic wasting disease.

The present invention also provides a method for treating or preventing a prion disease in a subject by administering to the subject an agent that binds to the Gln-Pro-His sequence of prion protein in an amount effective to treat or prevent the prion disease.

Furthermore, the present invention provides a method of inhibiting the dissemination of a disease condition caused by an infectious prion protein comprising inactivating streptavidin that may be contained in a physical substance by treating the physical substance with an amount of biotin, or a derivative thereof, effective to bind to the streptavidin, if present in the physical substance.

Finally, the present invention provides a method of treating a prion disease in a subject comprising administering to the subject an amount of biotin effective to treat the disease.

Additional objects of the invention will be apparent from the description which follows.

BRIEF DESCRIPTION OF THE FIGURES

FIG. 1 sets forth the results of a Western blot of scrapie infected brain. Lane 1 was probed with biotinylated 3F4 monoclonal antibody; Lane 2 with 3F4 antibody followed by phosphatase conjugated secondary antibody. Bands are detected at about 30 kDa, which is consistent with that of prion protein.

FIG. 2 sets forth the results of a Western blot of scrapie infected and non-infected brain homogenates. Lane 1 is non-infected brain extract which was probed with biotinylated 3F4 antibody and streptavidin-phosphatase. Lane 2 is infected brain extract which was probed as Lane 1. Lane 3 is non-infected brain extract probed with streptavidin-phosphatase only; Lane 4 is infected brain extract probed as Lane 3.

FIG. 3 sets forth the results of a Western blot of infected brain probed with streptavidin-phosphatase. Intense banding is seen at 30–34 kDa.

FIG. 4 shows the results of binding of streptavidin-phosphatase to resins. Spots A1 1–5 are a 3-fold serial dilution of the first column volume of the flow through, Spots A2 1–5 are a 3 fold serial dilution of the 2nd column volume of flow through. Spots Ea are a 3-fold serial dilution of the boitin eluted material.

FIG. 5A shows the effect of adding 0.2 ml of 100 $\mu$M biotin to 0.2 ml of streptavidin-phosphatase prior to the addition of resin A. The significant phosphatase activity shown in the flow through of the column suggests the lack of binding of streptavidin phosphatase to the resin. FIG. 5B shows the effect of adding 0.2 ml of streptavidin-phosphatase only prior to the addition of resin A. The small amount of streptavidin phosphatase present in the flow through column suggests that streptavidin phosphatase binds to resin A, indicating that biotin competes with the binding of streptavidin to the Gly-Tyr-Gly-Gln-Pro-His-Gly-Gly (SEQ ID NO: 1) sequence attached to resin A. CV=column volume (1 ml).

DETAILED DESCRIPTION OF THE INVENTION

Figure 1:
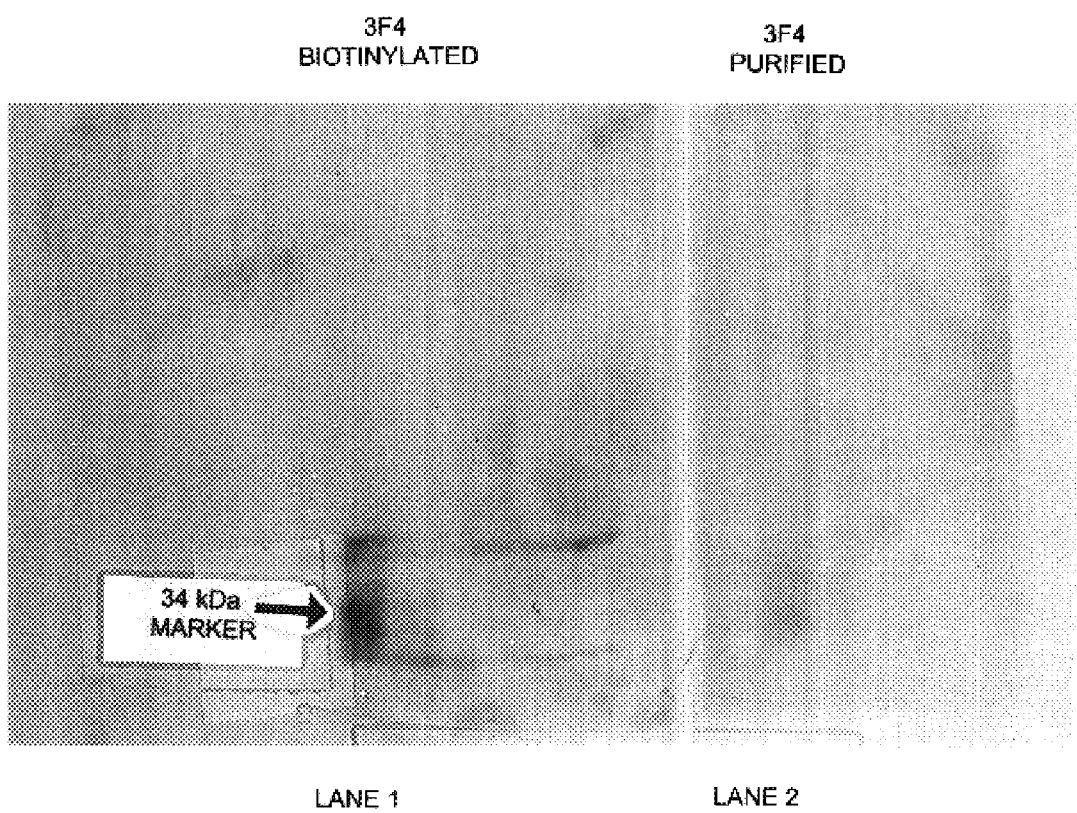
FIG. 1.

The present invention provides novel methods of detecting and isolating prion proteins, as well as methods for diagnosing and treating prion diseases.

Specifically, the present invention provides a method of detecting the presence of prion protein in a sample comprising contacting said sample with an agent which binds to the amino acid sequence Gln-Pro-His of prion protein and detecting said agent bound to said prion protein. As defined herein, "prion protein" may be a "normal" prion protein, also referred to as a "sensitive" prion protein, and may be designated "PrPc" protein. The prion protein may also be an infectious form of the protein, also called a "resistant" or "scrapie" form, and may be designated "PrP$^{sc}$" protein. Also included in the definition of prion protein are variants of the sensitive and resistant forms of the prion protein. Prion protein variants herein include all isoforms of both the sensitive and resistant forms and all isolates or strains of prion protein. The isolates or strains may vary by structure or conformation, or by characteristic incubation times of the disease, disease length and pathology. The amino acid sequences of the variants may also vary by one or more amino acids.

The agent employed in the method of detection of prion proteins may be a protein, peptide, polypeptide, nucleic acid, non-peptide organic molecule or organic reagent. An example of a protein that binds to the amino acid sequence Gln-Pro-His of prion protein is streptavidin. Streptavidin is tetravalent and is theoretically capable of binding from one to four prion protein molecules. The agent which binds to the prion protein may be attached to a detectable marker to facilitate the detection of prion protein in a sample. Non-limiting examples of detectable markers are fluorescence, enzyme, or radiolabeled markers, including $^{32}$P, and the like. In a preferred embodiment of the invention, the detectable marker is phosphatase. In this embodiment, the agent, such as streptavidin, is conjugated to phosphatase and the conjugated streptavidin is visualized by the addition of a substrate such as 5-bromo-4-chloro-3'-indolyphosphate p-toluidine salt/nitroblue tetrazolium chloride (BCIP/NBT). In another embodiment of the invention, streptavidin is added to the sample before, at the same time, or after the addition of one or more chelators of heavy metals. A chelator of a metal, such as CuII, may enhance the binding of streptavidin to prion protein.

The method of detection of prion protein provided by the present invention may be employed for the detection of prion protein in many different types of samples. For example, the sample may be blood, plasma, serum, cerebrospinal fluid, brain tissue, cornea tissue, urine, fecal matter, soil, bone meal, beef, beef by-products, sheep, sheep by-products, deer, deer by-products, elk, elk by-products, water or milk. Because bovine spongiform encephalopathy is transmitted to cows through feedstuff supplemented with beef or sheep by-products, a method for detecting prion proteins in material such as feedstuff is extremely useful. The method of detection of prion proteins provided herein may also detect prion proteins in brain tissue, which is extremely important for dura mater grafting.

Prion protein may be detected by the binding of an agent to the amino acid sequence Gln-Pro-His of prion protein in solution, followed by separation from non-bound agent using an affinity column or electrophoretic separation.

In solution, the agent which binds to the Gln-Pro-His sequence of prion protein is bound to a detectable marker and the presence of prion protein is simply visualized, or determined by measuring the optical density using a spectrophotometer.

Prion proteins may also be separated from other proteins in a sample by using an affinity column. In this instance, the agent which binds to the Gln-Pro-His sequence of prion protein is bound to a resin, and the prion protein which binds to the immobilized agent on the resin is eluted from the column and further purified. In a specific embodiment of the invention, streptavidin is bound to a resin, such as beaded agarose. Other types of resins that may be used include, but are not limited to, sepharose, cross-linked agarose, cross-linked DEAE agarose, toyopearl, composite cross-linked polysaccharides, Celite, acrylic beads, dextran beads, polystyrene beads and cellulose.

Prion proteins may also be separated from other proteins in a sample using electrophoretic separation on a gel. Examples of electrophoretic separation gels include polyacrylamide gel electrophoresis (PAGE), sodium dodecal sulfate (SDS)-PAGE and reducing SDS gels. In a particular embodiment of the invention, native PAGE is used to separate proteins by structure. The different forms of prion proteins, including the variants, can be separated based on their conformations by gels in the presence of urea. A dense molecule such as $PrP^{sc}$ is poorly denatured with low concentrations of urea, and thus will migrate faster than $PrP^{c}$ under conditions of denaturation of $PrP^{c}$ and retention of $PrP^{sc}$ structure. Transfer of the proteins onto nitrocellulose by Western blot techniques allows for the detection of the relative mobilities of $PrP^{c}$ and $PrP^{sc}$ through probing with agents which bind to the amino acid sequence Gln-Pro-His of prion protein.

Also provided by the present invention is a method of isolating prion protein in a sample comprising contacting said sample with an agent which binds to the amino acid sequence Gln-Pro-His of prion protein and isolating said agent bound to said prion protein. The isolation of prion protein may be achieved using the methods described above in combination with classical methods of purification commonly known to those of skill in the art, such as affinity chromatography on resins with immobilized antibodies specific for the prion. The inventors' unique discovery of an agent which binds to the amino acid sequence Gln-Pro-His of prion protein allows for the purification of native forms of $PrP^{c}$ and $PrP^{sc}$ protein which prior to this invention has not been reported.

Also provided by the present invention is a kit useful for detecting prion protein comprising an agent which binds to the amino acid sequence Gln-Pro-His of the prion protein. This is useful for the detection of prion protein in a sample and thus the diagnosis of prion diseases. The agent provided in the kit may be, for example, a protein, peptide, polypeptide, nucleic acid, non-peptide organic molecule, organic reagent, or a combination thereof. In a preferred embodiment of the invention, the agent is streptavidin, and is bound to a detectable marker, such as phosphatase.

Further provided by the present invention is a method for diagnosing a prion disease in a subject comprising the steps of: (a) contacting a biological sample from the subject with an agent which binds to the amino acid sequence Gln-Pro-His of prion protein; and (b) detecting formation of a complex between said prion protein and said agent, if present in said biological sample. The biological sample may be, for example, blood, plasma, serum, cerebrospinal fluid, brain tissue, cornea tissue, urine or fecal matter. The subject may be human or an animal. Non-limiting examples of prion diseases which may be diagnosed using the method of the present invention are Creutzfeld-Jakob disease, Gerstmann-Sträussler-Scheinker disease, fatal familial insomnia, scrapie, bovine spongiform encephalopathy (mad cow disease), transmissible mink encephalopathy, feline spongiform encephalopathy, exotic ungulate encephalopathy, and chronic wasting disease. Specific examples of Creutzfeld-Jakob disease which may be diagnosed using the method provided by the present invention include iatrogenic, variant, familial and sporadic Creutzfeld-Jakob disease.

The present invention further provides a method for treating a prion disease in a subject comprising administering to said subject an amount of an agent which binds to the amino acid sequence Gln-Pro-His of prion protein effective to treat or prevent the prion disease. The subject may be a human or an animal. The agent treats or prevents the prion disease by inhibiting the binding of streptavidin to prion protein and thus inhibiting the conversion of non-infectious prion protein to infectious prion protein. This may be accomplished by the binding of the agent to streptavidin or the binding of the agent to the prion protein, or a combination thereof. The streptavidin may be that which is already present in the subject at the time of administration of the agent to the subject, or that which is introduced from outside the subject. Streptavidin may be introduced into a subject by ingestion of or exposure to soil that contains streptavidin-releasing bacteria, such as Streptomyces. Streptavidin may also be present in a subject that has a bacterial infection. In a specific embodiment of the invention, an agent which binds to the amino acid sequence Gln-Pro-His of prion protein is administered together with biotin, or derivatives of biotin in amounts effective to treat the prion disease. The subject may be a human or an animal. Types of diseases which may be treated using the method provided by the present invention include, but are not limited to, Creutzfeld-Jakob disease, Gerstmann-Sträussler-Scheinker disease, fatal familial insomnia, scrapie, bovine spongiform encephalopathy (mad cow disease), transmissible mink encephalopathy, feline spongiform encephalopathy, exotic ungulate encephalopathy, and chronic wasting disease. Specific examples of Creutzfeld-Jakob disease which may be diagnosed using the method provided by the present invention include iatrogenic, variant, familial and sporadic Creutzfeld-Jakob disease.

Also provided by the present invention is a method of screening for an agent which binds to the amino acid sequence Gln-Pro-His of the human prion protein comprising detecting the presence of the agent bound to the prion protein. Methods by which agents that bind to the amino acid sequence Gln-Pro-His of the human prion protein may be screened are commonly known to one of skill in the art. For example, the peptide Gly-Tyr-Gly-Gln-Pro-His-Gly-Gly (SEQ ID NO: 1) (or prion protein) is bound to a resin and packed into a column. A sample containing a potential binding agent is run through the column, and those agents that bind to the Gly-Tyr-Gly-Gln-Pro-His-Gly-Gly (SEQ ID NO: 1) (or prion protein) are eluted and identified. In another embodiment, the peptide Gly-Tyr-Gly-Gln-Pro-His-Gly-Gly (SEQ ID NO: 1)(or prion protein) is immobilized on a microtiter plate, nitrocellulose, or other support. The sample containing the potential binding agent is added and incubated to allow the binding agent to bind to the immobilized peptide Gly-Tyr-Gly-Gln-Pro-His-Gly-Gly (or prion protein). Non-bound material is washed away.

The present invention further provides agents which bind to the amino acid sequence Gln-Pro-His of prion protein, thereby inhibiting the occurrence or progression of prion diseases. Agents that bind to the prion protein may be sterochemically designed so that, based upon the structure and characteristics of the Gln-Pro-His of prion protein, they will bind to the sequence.

The inventors have found that streptavidin binds to the Gln-Pro-His sequences of the prion protein. By using this finding, agents which mimic the binding of streptavidin can be designed. The prion protein has four Gln-Pro-His sequences, each of which is located near one or more glycines. Peptides rich in glycine and proline will not form alpha helices or beta sheets. This sequence is unlikely to have any secondary structure (Miura, et al. FEBS Lett. 396:248–252 (1996)). For these reasons, one of skill in the art would not target the octapeptide Gly-Tyr-Gly-Gln-Pro-His-Gly-Gly (SEQ ID NO: 1) sequence as a binding site. Indeed, no one has reported targeting the Gln-Pro-His sequence as a binding site. The closest report is one describing the interaction of streptavidin with His-Pro-Gln sequences (Weber, et al. Biochem. 31:9350–9354 (1992)). Agents which mimic the binding of streptavidin to prion protein may be designed using available x-ray crystallography and NMR data of streptavidin, as well as available data of the streptavidin-biotin complex. Crystallography data of streptavidin and streptavidin bound to various ligands may be found, for example, in Katz, *Biochemistry* 34:7 15421–15429 (1995) and Avilar-Sakar and Chiu, *Biophysical Journal* 70:57–68 (1996).

The inventors herein hypothesize that in order for a normal, or sensitive prion protein to be converted to an infectious, or resistant prion protein, the two proteins must be in close proximity to one another. It is likely that two prion proteins are brought together by a "chaperon" which binds to prion protein and facilitates the conversion of sensitive to resistant prion protein. The inventors have found that streptavidin binds tightly to the Gln-Pro-His sequences of the prion protein. Since streptavidin is a tetrameric protein, it can theoretically bind up to four prion proteins, positioning them in close proximity with one another. The ability of streptavidin to bind to two prion proteins allows for the interaction of the two prion proteins to be studied to determine how a sensitive prion protein is converted to a resistant prion protein. The binding capabilities of streptavidin to prion protein also provides a basis for developing and detecting chaperones that bind to prion proteins by, for example, a competition ELISA. In this example prion protein is first immobilized onto a microtiter plate, nitrocellulose, or other support. The sample containing a potential chaperon is then added and incubated to allow the chaperon to bind to the prion protein. Streptavidin-phosphatase is then added and allowed to bind to the prion protein. Non-bound streptavidin-phosphatase is washed away and the amount bound is measured by the addition of substrate for phosphatase. Binding of streptavidin will be competed for by agents binding at the same site. Thus, the presence of chaperones, PrP binding bacteria, etc. can be detected by an inhibition of phosphatase enzyme activity.

Accordingly, the present invention further provides for a method for screening for an agent that binds to two or more prion proteins comprising the steps of (1) combining infectious and non-infectious prion protein to form a protein mixture; (2) adding to the protein a sample containing a potential agent that binds to two or more prion proteins; and (3) comparing the resulting levels of infectious and non-infectious prion protein to the initial levels combined. The resulting levels of infectious and non-infectious prion proteins can be determined by the changes in mobility of the proteins on a urea gel, and the amounts determined relative to controlled amounts. A greater amount of infectious prion protein present in the resulting protein mixture than the amount initially added is indicative of a conversion by a chaperone of non-infectious to infectious prion protein, and indicates that a chaperone is present in the test sample. The amount of infectious prion protein present in the resulting protein mixture may also be determined by protease resistance experiments and infectivity studies where the resulting mixture is injected into a research animal and observed for signs of prion diseases. A sample containing a potential agent that binds to two or more prion proteins may also be identified using a sandwich ELISA assay. In this instance, the peptide Gly-Tyr-Gly-Gln-Pro-His-Gly-Gly (SEQ ID NO: 1) (or prion protein) is immobilized on an ELISA plate, the sample containing a potential agent that binds to two or more prion proteins is added to the plate, radiolabeled peptide Gly-Tyr-Gly-Gln-Pro-His-Gly-Gly (SEQ ID NO: 1) (or prion protein) is added to the plate, and the non-bound material is washed away. An agent which binds to both the immobilized peptide Gly-Tyr-Gly-Gln-Pro-His-Gly-Gly (SEQ ID NO: 1) (or prion protein) and the radiolabeled peptide Gly-Tyr-Gly-Gln-Pro-His-Gly-Gly (SEQ ID NO: 1) (or prion protein) is then identified.

The inventors have also discovered (unpublished data) that biotin, by binding to streptavidin, can prevent the binding of streptavidin to prion proteins and thus could prevent the conversion of a sensitive prion protein to a resistant prion protein. Binding of streptavidin to prion protein is thought to be mediated through a site on streptavidin which uses the same amino acids as biotin. Thus, it can be competed for by biotin. Biotin may therefore be used in inhibiting the association of prion protein with streptavidin. Since biotin may effectively inhibit the conversion of sensitive prion protein to resistant prion protein, biotin may be used to inhibit the dissemination of prion disease. The interactions of biotin, streptavidin and prion protein also provide an extremely useful model for designing agents that inhibit the spread of infectious prion protein in a tissue.

Accordingly, the present invention provides for a method of inhibiting the dissemination of a disease condition caused by an infectious prion protein comprising inactivating streptavidin that may be contained in a physical substance by treating the physical substance with an amount of biotin, or a derivative thereof, effective to bind to the streptavidin, if present in the physical substance. A "physical substance" is herein defined as a physical material which has discrete existence. The physical substance may be a liquid or a solid substance. The liquid substance may be, for example, water, milk, and juice. The solid substance may be, for example, meat, meat by-products, animal feed, and soil. When a physical substance is treated with biotin, the biotin will bind to the bacterial protein streptavidin. Thus, when the physical substance treated with biotin is ingested by a human or an animal, the streptavidin will be bound by biotin and will be unable to aid in the conversion of native prion protein to infectious prion protein.

As used herein, "treating" a liquid or a solid is achieved by adding the biotin to the liquid or solid and includes contacting the liquid or solid with biotin. The biotin may be added to liquids such as, for example, water, milk and juice. The biotin, or derivative thereof, may be added to a water supply system, or a water supply. Non-limiting examples of water supplies which may be supplemented with biotin include water wells, ponds, lakes, springs, reservoirs, swimming pools, cisterns, water troughs, and water tanks. Non-limiting examples of solids which biotin may be added to include all cuts and types of meat, such as beef, chicken, pork, turkey and lamb, and all types of animal feed.

The method of inhibiting the dissemination of a prion disease provided herein may be used to inhibit dissemination of such diseases as Creutzfeld-Jakob disease, variant Creutzfeld-Jakob disease, Gerstmann-Sträussler-Scheinker disease, fatal familial insomnia, scrapie, bovine spongiform encephalopathy (mad cow disease), transmissible mink encephalopathy, feline spongiform encephalopathy, exotic ungulate encephalopathy, and chronic wasting disease.

Biotin may be in the form of a liquid or solid, such as a crystalline. Derivatives of biotin may also be employed in the method described herein. Non-limiting examples of derivatives of biotin which may be used include D-biotin, biotin 4-amidobenzoic acid, biotinamidocaproate. n-hydroxysuccinimide ester, biotinamidocaproic acid 3-sulfo-n-hydroxy-succinimide ester, 6-(biotinamidocaproylamido)-caproic acid N-hydroxy-succinimide ester, biotinamidocaproylhydrazine, biotin 6-amidoquinoline, biotin-dextran, biotin disulfide n-hydroxy-succinimide ester, biotin hydrazine, d-biotin n-hydroxysuccinimide ester, biotin methyl ester, biotin malamide, d-biotin p-nitrophenyl ester, biotin-propanolol analog, sulfosuccinimidyl biotin, biotinyl-Asp-Glu-Val-Aspartin-1-Al, biotinyl-Asp-Glu-Val-L-Aspartic acid aldehyde, photobiotin, biocytin, diaminobiotin, biocytinamide, n-hydroxysuccinimidobiotin and 2-iminobiotin.

In a specific embodiment of the invention, D-biotin is used to inhibit the dissemination of prion disease such as scrapie, mad cow disease, and other forms of spongiform encephalopathies. In another embodiment of the invention, biotin is added or applied to meat and meat by-products during slaughter, manufacturing and/or packaging. In another embodiment, biotin is added to dressings, flavorings, marinates, and sauces for direct application to meat before, during, and/or after cooking. In another embodiment of the invention, biotin is packaged and sold in a liquid form, or a solid form that dissolves easily in liquids, which may then be added directly to the water troughs of animals. This liquid form of biotin may also be added dropwise to drinks and food before ingesting.

The method of inhibiting the dissemination of a disease condition caused by an infectious prion protein comprising inactivating streptavidin that may be contained in a physical substance by treating the physical substance with an amount of biotin, or a derivative thereof, effective to bind to the streptavidin, may further comprise the addition of other inhibitors that inhibit the conversion of $PrP^c$ to $PrP^{sc}$.

The present invention also provides a method for treating or preventing a prion disease in a subject comprising administering to the subject an amount of biotin, or a derivative thereof, effective to treat or prevent the prion disease in the subject. The subject may be a human or an animal.

The prion diseases which may be treated by the method of the present invention include, but are not limited to, Creutzfeld-Jakob disease, variant Creutzfeld-Jakob disease, Gerstmann-Sträussler-Scheinker disease, fatal familial insomnia, scrapie, bovine spongiform encephalopathy (mad cow disease), transmissible mink encephalopathy, feline spongiform encephalopathy, exotic ungulate encephalopathy, and chronic wasting disease.

The biotin, or derivative thereof, which is administered to the subject to treat a prion disease may be administered intravenously or by ingestion.

It has been postulated that bacteria are responsible for prion diseases, but no data has been provided to support this theory. It is not known why sheep can be grazed on soil that has no history of exposure to infectious prion proteins or sheep grazing and the sheep still contract scrapie. The inventors herein theorize that, because of the ability of streptavidin to convert a native prion protein to an infectious prion protein, the sheep may have contracted scrapie through the ingestion of or exposure to soil that contains streptavidin-producing bacteria.

The progression of a prion disease in its subject is usually a slow process. After inoculation of infectious prion protein in a research subject, it takes at least six months or more to develop the full pathogenesis. This rate of pathogenesis ensures that research proceeds at a slow pace. The invention provided herein establishes that streptavidin binds together two prion proteins, allowing for a normal, or sensitive prion protein to be converted to an infectious, or resistant prion protein. Accordingly, the addition of streptavidin or streptavidin-producing bacteria to the inoculation of an infectious prion protein in a research subject should facilitate the conversion of native prion protein to infectious prion protein, which may increase the rate of pathogenesis of a prion disease and allow for research to progress at a much faster pace.

The present invention is described in the following Experimental Details Section, which is set forth to aid in an understanding of the invention, and should not be construed to limit in any way the invention as defined in the claims which follow thereafter.

Experimental Details Section

I. Materials and Methods

Brain homogenates were prepared from scrapie (SSBP1 from Cheviot sheep) infected hamsters and were provided by MA BioService, Rockville, Md. In brief, they were prepared as a pool of eight infected brains from Golden Syrian Hamsters. A 10% homogenate was made and large aggregates were removed by low speed centrifugation. Brains from non-infected hamsters were obtained from Charles River. They were homogenized as a 10% suspension and large aggregates were removed by low speed centrifugation.

Peptides were synthesized by standard fmoc chemistry directly onto Toyopearl AF-amino 650 M resin (TosoHaas, Montgomeryville, Pa.) by Commonwealth Biotechnologies Inc. of Richmond, Va. The following peptides were synthesized: (A) acetylated Gly-Tyr-Gly-Gln-Pro-His-Gly-Gly—, (SEQ ID NO: 1), (B) acetylated Gly-His-Gly-Gln-Gly-Pro-Gly-Tyr— (SEQ ID NO: 2), (C) Toyopearl resin without peptide, and (D) amino Thr-Pro-His-Pro-Gln-Gly— (SEQ ID NO: 3).

3F4 monoclonal antibodies were obtained from Senetek (St. Louis, Mo.). These antibodies recognize the internal sequence Met-Lys-His-Met (SEQ ID NO: 4) of hamster and human prion protein. Streptavidin-phosphatase, D-biotin and goat anti-mouse IgG antibody-phosphatase conjugate were from Sigma. The nitrocellulose was from Schleicher and Schuell, pre-caste SDS-PAGE gels were from Novex, molecular weight standards and all chemical reagents were of analytical grade or higher and were from Sigma. Chemiluminescent substrate was from Tropix (MA) catalog number MS025.

Western Blots. Western blots were performed using 4–20% reducing SDS-PAGE gel. Protein was mixed in SDS-PAGE loading buffer and heated at 95° C. for 5 mins. In some experiments 5% beta mercaptoethanol was present to reduce the disulfide bonds. Typically, 10 μl of protein solution was added to each lane of a 10 lane pre-caste SDS-PAGE gel. Some gels were stained with Coomassie blue according to standard methodologies. Proteins from other gels were electrophoretically transferred to nitrocellulose. Following transfer the non-specific binding sites on the nitrocellulose were blocked with 1.0% (W/V) casein solution (Pierce) in 0.05 M Tris, 0.15 M NaCl pH 7.4. After blocking, the immobilized protein was probed with solutions containing antibodies or streptavidin-phosphatase in 1% casein with gentle rocking for either 16–20 hours for primary antibodies or streptavidin-phosphatase for 45 mins. Probing conditions were varied according to the individual experiments. After the primary antibody, the secondary detection system was added and incubated for 45 minutes. The secondary detection system was either alkaline phosphatase conjugated goat anti mouse IgG for primary 3F4 monoclonal antibody or streptavidin-phosphatase for biotinylated 3F4 monoclonal antibody. After incubation the nitrocellulose was washed 6× with TS plus 0.05% (w/v) Tween 20 and 6× in TS. Whereupon the nitrocellulose was equilibrated in 0.05 M Tris, 5 mM $MgCl_2$ pH 9.5 (TM) for 5 minutes. The nitrocellulose was allowed to drip dry and was then equilibrated with TM containing 0.25 mM phosphatase chemiluminescent substrate from Tropix. The nitrocellulose was wrapped in seal wrap and placed into an autoradiography cassette and, in the dark, was over layed with X-ray film. The phosphatase was allowed to react with substrate at room temperature before the exposed film was developed. The faint outlines of the nitrocellulose on the film facilitated accurate alignment of the molecular weight markers.

Resins. The resins, typically 0.5 to 1 ml, were packed into Poly-Prep™ chromatography columns (Bio-Rad). They were first washed with 6M urea, followed by 2% acetic acid in 70% alcohol. The resins were equilibrated to pH 8.0 with 0.05 M Tris, 0.15 M NaCl pH 8.0 (TS). Solutions containing streptavidin-phosphatase were added to the resin and allowed to enter the gel. The flow rate was stopped for 15 mins after which time the resin was washed with TS. One column volume aliquots of the eluate were collected for a total of 10 column volumes. In examples where the material was eluted with biotin, biotin was added at a concentration of 10 μM in a total volume of 2 mls (2 column volumes). The flow rate was stopped and the resin was resuspended and allowed to stand at room temperature for 15 minutes. The solution plus eluted protein was allowed to elute from the column and was collected in total. For analysis of streptavidin binding the conjugated phosphatase enzyme was assayed by dot blot.

Phosphatase dot blot. 5 or 10 μl aliquots of solution were spotted onto a piece of nitrocellulose. The spot was allowed to dry and the nitrocellulose was moistened with TM plus phosphatase substrate. The substrate was allowed to permeate the nitrocellulose for 10 minutes before the nitrocellulose was drip dried, wrapped in film and overlayed and developed according to the Western methodology.

II. Results

The results of the Western blot are shown in FIG. 1. Specifically, a Western blot of protein from scrapie infected brain was probed with lane 1 biotinylated 3F4 monoclonal antibody for 16–20 hours at 4° C. then washed twice for 10 mins in TS and incubated with 1/1000 fold diluted streptavidin-phosphatase stock solution for 45 minutes. Washing and detection was as presented in the Materials and Methods. Lane 2 was probed with 3F4 antibody for 16–20 hours followed by washing then incubation with phosphatase conjugated secondary antibody. Following exposure of the film for 1 minute, bands at about 30 kDa could be easily detected. Film following 10 minutes exposure is seen in FIG. 1. These results indicate that 3F4 antibody recognizes proteins of molecular weight about 30 kDa as anticipated and is consistent with that of prion protein.

Figure 2:
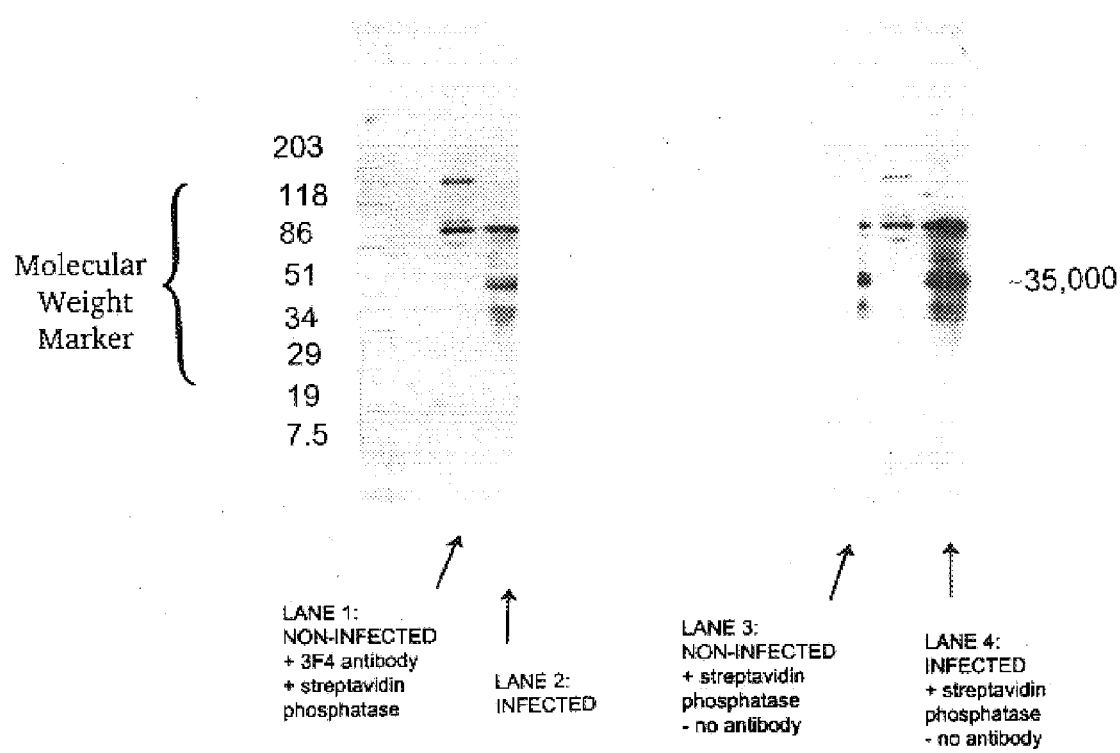
FIG. 2.

The results of a Western blot containing protein from scrapie infected and non-infected brain homogenates is shown in FIG. 2. Lane 1 was non-infected brain extract probed with biotinylated 3F4 antibody and streptavidin-phosphatase. This shows a band of molecular weight about 86 kDa and a higher molecular weight band of above 118 kDa. The lower band of 86 kDa molecular weight is present in both non-infected and extracts of infected brain when probed in a similar manner (lane 2). The higher molecular weight band is missing in the infected brain, however, there appears additional bands of molecular weight 51 kDa and about 30–34 kDa. The lower molecular weight bands are of equivalent molecular weight to prion protein. In the absence of 3F4 antibody an identical pattern is seen in lane 3 for uninfected and lane 4 for infected brain extracts. The lower molecular weight bands of about 34 kDa molecular weight show multiple bands of similar molecular weight consistent with the different glycosylated forms of the prion protein. Thus, the bands at about 34 kDa molecular weight are only present in the infected brain and are probably the different glycosylated forms of the prion protein.

Figure 3:
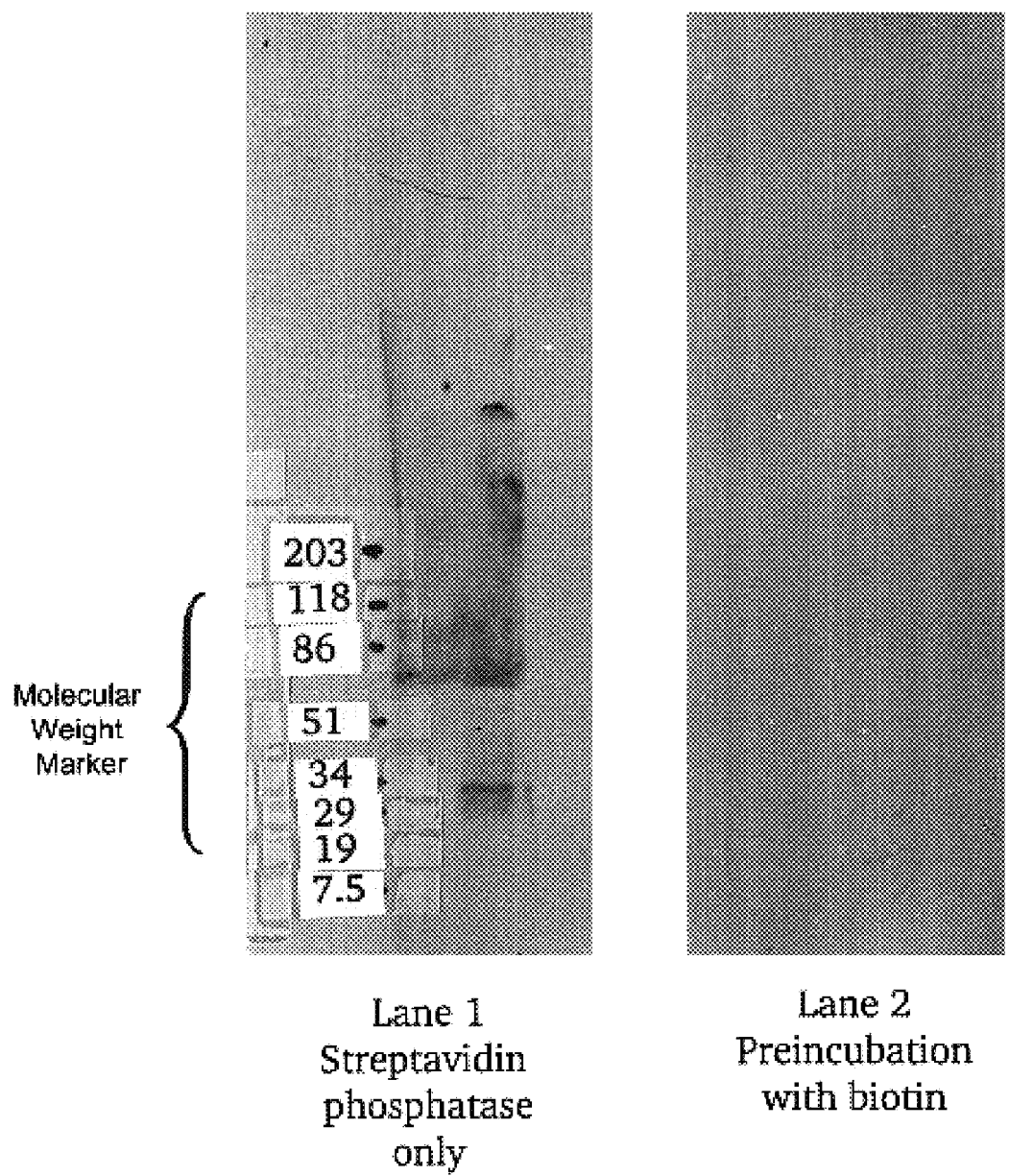
FIG. 3.

An extract of infected brain was probed with streptavidin-phosphatase and showed intense banding at 29–34 kDa. These results are set forth in FIG. 3. Lane 1 shows the banding pattern with streptavidin-phosphatase with bands at 30–34 kDa. Lane 2 shows the same conditions except that the streptavidin-phosphatase was mixed with 10 μM D-biotin prior to addition to the Western blot. Under these conditions the banding at 30–34 kDa was completely inhibited by the presence of D-biotin. It was noted that if D-biotin was added after binding of streptavidin to the proteins biotin did not compete with the production of signal. Thus, biotin competes for the ability of streptavidin to bind to the prion protein, but is not strong enough to displace easily already bound streptavidin-phosphatase conjugate. Streptavidin therefore binds through a site that can be competed for by biotin.

Figure 4:
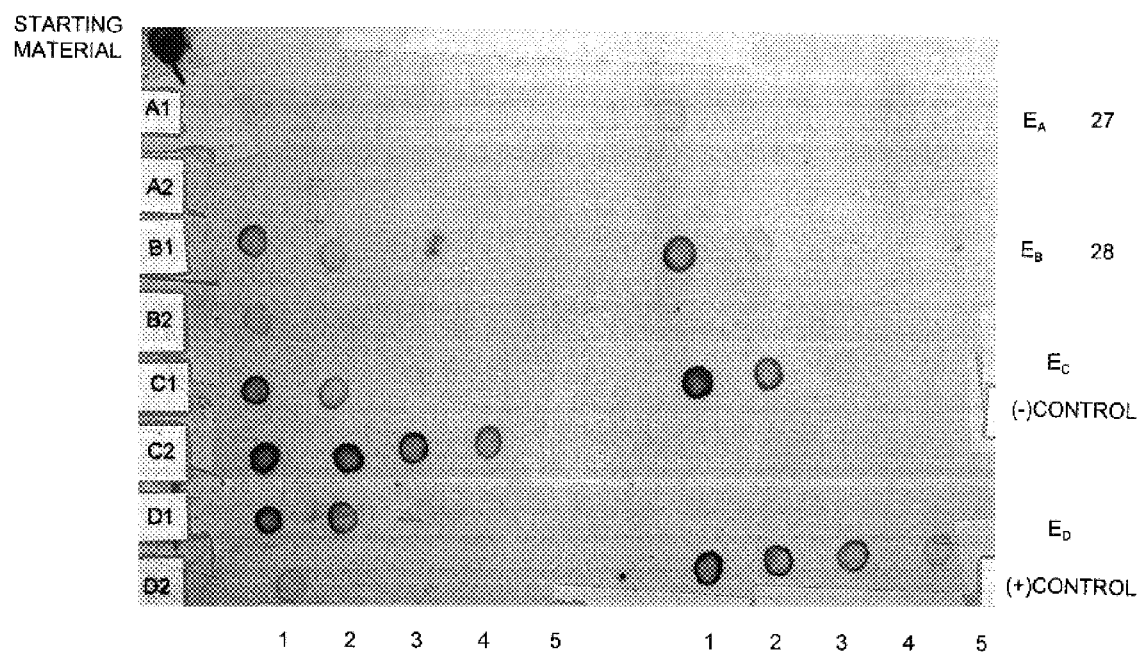
FIG. 4.

The binding of streptavidin-phosphatase to resins was also demonstrated (see FIG. 4). Spots A 1–5 are a 3-fold serial dilution of the first column volume of the flow through of resin A (see Methods). Spots A 2 1–5 are a 3 fold serial dilution of the 2nd column volume of the flow through. Spots Ea are a 3-fold serial dilution of the biotin eluted material. From resin A it can be seen that very little activity was found associated with the first, second column volumes of the flow through (A1 and A2) or was released with biotin. A similar evaluation was performed for resin B. More phosphatase activity was found associated with the flow through fractions B1 and B2 and more was eluted in biotin Eb. Resin C behaved differently, much more activity was found in the flow through C1 and C2, in particular the second column volume. Additional phosphatase was eluted with biotin. This resin behaved like a weak binder (ion exchange) for streptavidin. Considerably more phosphatase was removed from this resin than resins A and B. Resin D contained the internal His-Pro-Gln sequence and was selected as a streptavidin binder (Lam, et al. Nature 354:82–84 (1991)). It bound a large percentage of the streptavidin-phosphatase and eluted considerable amounts of phosphatase in the presence of biotin. Thus, the sequence Gly-Tyr-Gly-Gln-Pro-His-Gly-Gly (SEQ ID NO: 1) of the prion protein binds streptavidin (resin A), but its binding cannot be easily competed for by biotin. This is similar to the situation for the ready bound streptavidin-phosphatase conjugates in the Western blot studies.

Figure 5A:
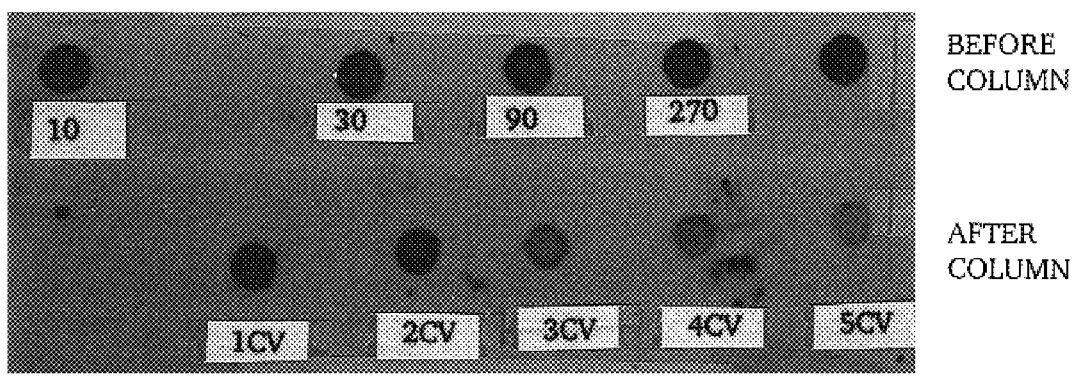
FIGS. 5A and 5B.
Figure 5B:
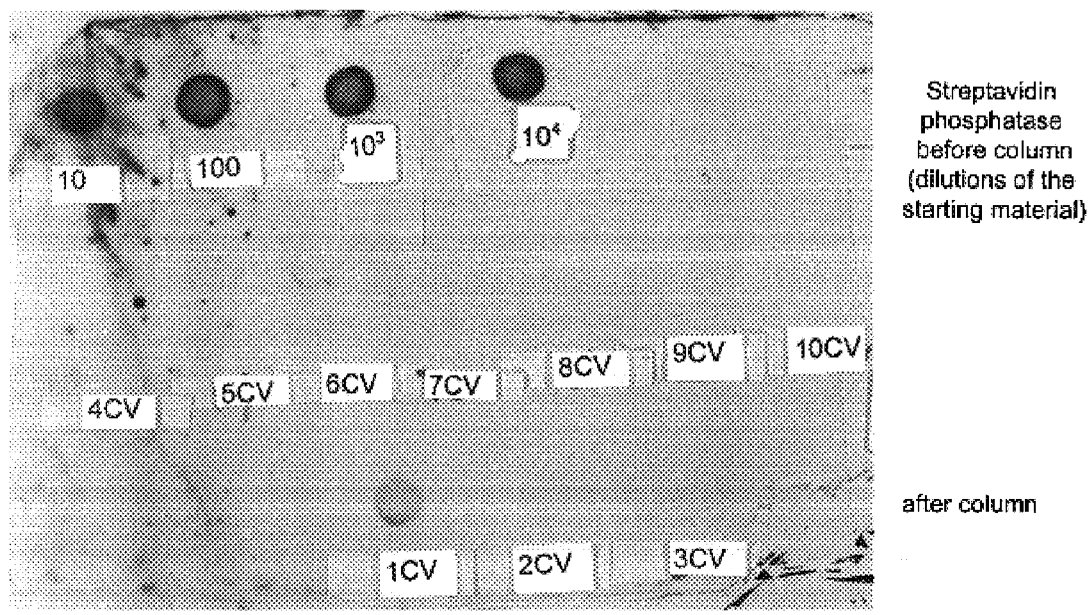

The effect of pre-incubation of biotin with streptavidin-phosphatase and its subsequent binding to resin A is shown in FIG. 5. 0.2 ml of 100 $\mu$M biotin was added to 0.2 ml of streptavidin-phosphatase prior to the addition to resin A. In this situation each column volume of TS was collected and assayed for phosphatase activity. The activity was found in the first few column volumes washing from the column. In contrast, in the absence of biotin, the vast majority of the applied streptavidin-phosphatase was stuck to the column and did not wash through. This result demonstrates that the interaction of the streptavidin with the repeat sequence within the prion protein is mediated through a specific interaction that can be competed for by prior exposure of the streptavidin to biotin. Thus, it is consistent with the Western blot data.

III. Discussion

Streptavidin binds to proteins of molecular weight identical to prion proteins and present in infected, but not uninfected brains. Binding can be competed for by prior exposure of the streptavidin to biotin, suggesting that the interaction was mediated through a site similar to the His-Pro-Gln binding site of streptavidin. The octapeptide repeat sequence of prion protein Gly-Tyr-Gly-Gln-Pro-His-Gly-Gly (SEQ ID NO: 1) when synthesized on resin will bind streptavidin. The binding is not effectively inhibited by biotin once it has occurred, but is effectively inhibited by prior exposure of the streptavidin to the biotin. Taken together, these results indicate that prion protein binds tightly and specifically to streptavidin through the repeated Gly-Tyr-Gly-Gln-Pro-His-Gly-Gly (SEQ ID NO: 1) sequence present in the prion protein and a site in streptavidin.

Streptavidin is a protein used extensively in biochemical research. It is a biotin binding protein secreted by *Streptomyces avidinii*. Species of streptomyces are soil dwelling bacteria that can cause infection. Streptavidin binds with very high affinity (~$10^{15}$) to biotin. Biotinylation of proteins and nucleotides through chemical modification facilitates the detection and recovery of these entities following various manipulations. This is accomplished by adding streptavidin-enzyme conjugates. The streptavidin binds to the biotin which can then be identified by adding a substrate for the enzyme. A frequently used example is the biotinylation of nucleotide primers which are incorporated into larger strands of DNA by the use of the polymerase chain reaction. DNA can then be separated by agarose electrophoresis, then transferred onto nitrocellulose by a process referred to as Southern blotting. The presence of biotinylated primers incorporated into larger strands of DNA can then be visualized by adding streptavidin-phosphatase and, after washing to remove non-bound streptavidin phosphatase, the presence of bound phosphatase can be visualized with the addition of substrate. Frequently used substrates include BCIP/NBT, which produces a colored product in the presence of phosphatase and substrates which produce light (Masecar, et al. in Phage Display of Peptides and Proteins 293–303 (1996)).

Proteins such as the monoclonal antibody 3F4 may also be biotinylated. The monoclonal antibody binds to the prion protein, but not to fibrils of PrP$^{sc}$. Biotinylated 3F4 can then be used to detect the presence of target (prion) protein immobilized on inert supports such as nitrocellulose. First the antibody is incubated with the immobilized protein, then surplus or weakly bound antibody is removed by extensive washing. This is followed by the addition of streptavidin phosphatase which binds to biotinylated antibody and the surplus is removed by washing. Identification of prion protein is then mediated through the enzyme alkaline phosphatase in the presence of substrates. No reports exist for the detection of prion protein directly in the presence of streptavidin-phosphatase and without the mediation of antibodies.

The screening of combinatorial libraries revealed that peptides containing the sequence His-Pro-Gln bound to streptavidin and binding was competed for by D-biotin, suggesting that His-Pro-Gln bound to, or close to, the biotin binding site (Lam, et al. *Nature* 354:82–84 (1991), Devlin, et al. *Science* 249:404–406 (1990), and Weber, et al. *Biochem.* 31:9350–9354 (1992)). That the sequence Gln-His-Pro could bind to streptavidin was neither found nor predicted from the screening of combinatorial libraries. Thus, the discovery that the sequence Gln-His-Pro can bind to streptavidin was a surprising and unexpected finding. The reason for the lack of identification of binding sequences to Gln-Pro-His is not known, but may be due to the following considerations. Lam, et al. used 5 amino acid long peptides immobilized on beads. Each peptide was composed of L-amino acids and had a positive charge on the terminal amino acid. It is possible that His-Pro-Gln could not bind to streptavidin if a positive charge were in close proximity of the Gln. Thus, the sequence Gln-Pro-His may not have been detected by Lam, et al. since Gln would be close to the end terminal positive charge. In agreement with this hypothesis, Lam, et al. did not discover any His-Pro-Gln sequences that had a positively charged amino acid adjacent to the Gln. It should be noted that the prion protein has no positively charged amino acids within close proximity of the Gln in the octapeptide repeat. It is also possible that the side chains of amino acids present adjacent to the Gln-His-Pro could inhibit the binding of this sequence by steric hindrance. In this context it is important to note that the prion octapeptide repeat sequence has four glycines, one to the amino side of the Gln and three to the amino side of the His. Stereochemically, glycine has only one isomer and the side group of a single hydrogen is the least bulky of all amino acid side chains. Thus, it is possible that the glycine flanking sequences may have a role to play in the interaction. It is also possible that Lam, et al. did not identify the repeat unit of the prion consensus sequence as being a streptavidin binding sequence because this repeat is 8 amino acids long while the libraries screened by Lam were only 5 amino acids in length.

Devlin, et al. screened a phage library for binding sequences to streptavidin. These libraries were 15 amino acids in length, but contained only a minute fraction ($2\times10^7$) of all the possible ($20^{15}$) amino acid sequences. Thus, the chances of generating an individual clone containing the prion consensus would be remote. Devlin, et al. found several clones containing the sequence His-Pro-Gln, but no sequences containing Gln-Pro-His. The screening process used by Devlin, et al. requires elution of phage at low pH. The strongest binding sequences may not have been discovered due to their lack of recovery during screening.

Affinity resins containing ligands with the sequence His-Pro-Gln could be used to selectively bind streptavidin from complex media such as plasma (Baumbach and Hammond, Bio-Pharm May 24–35 (1992)). Elution of the bound streptavidin was possible by adding biotin to compete for binding with the His-Pro-Gln. However, the ability to purify proteins with naturally occurring sequences of Gln-Pro-His was not reported. Recombinant proteins with the sequence His-Pro-Gln (Schmidt and Skerra, *Protein Engineering* 6:109–122 (1993)) engineered into the protein could be purified by the use of immobilized streptavidin and eluted with biotin. However, there are no reports of any attempt to use the reverse structure Gln-Pro-His.

The nature of the interaction between streptavidin and the peptide sequences Phe-Ser-His-Pro-Gln-Asn-Thr (SEQ ID NO: 5) and His-Asp-His-Pro-Gln-Asn-Leu (SEQ ID NO: 6) was studied (Weber, et al. Biochem. 31:9350–9354 (1992)). The crystal structure of streptavidin complexed with one of these peptides was resolved to 2.0-A resolution. The peptide Phe-Ser-His-Pro-Gln-Asn-Thr (SEQ ID NO: 5) binds in a turn conformation with the histidine, proline and glutamine side chains oriented inward at the biotin binding site. A water molecule is immobilized between the histidine and glutamine side chains of the peptide and an aspartate acid side chain of streptavidin. Although some of the residues that participate in binding biotin also interact with the screened peptide, the peptide adopts an alternative method of utilizing binding determinants in the biotin-binding site. The Pro molecule provided the correct spacing between His and Gln, but was not directly involved in the interaction. Data bases were screened for the presence of the His-Pro-Glu sequences and one protein aspartate transcarbamylase which had a single occurrence and another citrate synthase had one His-Pro-Met were identified. The surrounding amino acids were considered to be unfavorable to the binding of these proteins to streptavidin. There are no reports of screening for the reverse sequence Gln-Pro-His. It is anticipated that peptides rich in glycine and proline will not form alpha helices or beta sheets. Since Gln-Pro-His is present in the prion protein in quadruplicate, this allows the possibility that multiple interactions could exist between prion protein and the tetrameric streptavidin molecule. Moreover, this region of the protein is accessible to interacting with ligands, therefore this region of the prion protein is particularly suitable for affinity chromatographic separation of both PrP$^c$, PrP$^{sc}$, and structural intermediates.

The structure of reverse sequences of peptides are essentially identical to each other only in the event they are composed of different enantiomers. For example, —D-Gln-D-Pro-D-His— will be comparable to —L-His-L-Pro-L-Gln—. These are referred to as retroinverso peptide analogs. When —L-Gln-L-Pro-L-His is compared to L-His-L-Pro-L-Gln, the side groups of the glutamine and histidine which are involved in binding streptavidin will be in the same relative position to each other. However, the connecting polypeptide bonds and the praline will not be similar to each other.

Purification of prion protein can be achieved by classical methods and affinity chromatography on resins with immobilized antibodies specific for the prion protein.

Separation of proteins may be achieved by a variety of methods, including polyacrylamide gel electrophoresis (PAGE). State-of-the-art techniques include reducing SDS-PAGE, non-reducing SDS-PAGE and native PAGE. In a particular variation of native PAGE, proteins can be separated according to structure. Both alpha 1 proteinase inhibitor and PrP share a common feature. The native form of alpha 1 proteinase inhibitor is rich in alpha helical structures which upon denaturation of proteolytic cleaving by elastase, the molecule adopts a structure with much greater beta sheet content and becomes resistant to denaturation by heat (Wright, *BioEssays* 18:453–464 (1996)). The two forms of alpha 1 proteinase inhibitor can be readily separated by PAGE (Mast, et al. *Biochem.* 31:2720–2728 (1992) and Lomas, et al. *J. Biol. Chem.* 270:5282–5288 (1995)). The more compact inactive structure migrates faster due to its higher charge/volume ratio than the more open non-activated form. By adding urea to the gel, the easily denatured form of the protein will be denatured and will adopt a more open structure and its migration will be retarded. The compact inactive alpha 1 proteinase inhibitor will migrate as a compact structure at a faster mobility than the denatured structure, thus the 2 forms can be resolved. Consequently, proteins, including the different forms of prion proteins with different conformations, can be separated by native gels in the presence of urea. A dense molecule such as $PrP^{sc}$ is poorly inactivated with low concentrations of urea and will thus migrate faster than $PrP^c$. PAGE of $PrP^c$ and $PrP^{sc}$ under conditions of denaturation of $PrP^c$ will result in faster migration of $PrP^{sc}$ relative to $PrP^c$. Transfer of the proteins onto nitrocellulose by Western blot techniques will allow detection of the relative mobilities of $PrP^{sc}$ and $PrP^c$ through probing with streptavidin-phosphatase conjugates. Thus, a method of detection of $PrP^{sc}$ in the presence of $PrP^c$ involves the separation of $PrP^c$ and $PrP^{sc}$ based upon structural considerations and detection of the two (or more) structures by binding to streptavidin-phosphatase. This method of using a non-denaturing gel to separate $PrP^c$ and $PrP^{sc}$ has not been previously reported or predicted.

Screening for new ligands to the prion protein may be accomplished by various methods (Devlin, et al. *Science* 249:404–406 (1990) and Lam, et al. *Nature* 354:82–84 (1991)). By knowing that the prion protein binds to streptavidin, a solid phase combinatorial library can be screened for binding sequence to streptavidin-phosphatase. The beads can then be screened for binding sequences to prion protein and streptavidin-phosphatase. Beads that bind only to prion protein and streptavidin-phosphatase and not to streptavidin-phosphatase alone can then be identified. The deduced structures on the beads can then be synthesized and used as ligands or inhibitors to prion protein. In the event the binding sequence is a linear peptide, the sequence can be encoded onto the sequence of streptavidin. This will permit a new structure to be designed that has the 4 repeats of the Gln-Pro-His binding structure, but also will contain the new and extra high affinity binding site to prion protein. The net result of these multiple interactions is a ligand with exceptional binding strength. Thus, structures deduced from libraries as bound to streptavidin may be used for stronger binding to the prion protein.

All publications mentioned hereinabove are hereby incorporated by reference in their entirety. While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. A method of detecting the presence of prion protein in a sample comprising contacting said sample with streptavidin and detecting streptavidin bound to said prion protein.

2. The method of claim 1 wherein the prion protein is $PrP^c$ protein, $PrP^{sc}$ protein, or a variant thereof.

3. The method of claim 1 wherein the streptavidin is bound to a detectable marker.

4. The method of claim 3 wherein the detectable marker is selected from the group consisting of a fluorescence marker, an enzyme, and a radiolabeled marker.

5. The method of claim 4 wherein the detectable marker is an enzyme, and the enzyme is phosphatase.

6. The method of claim 1 wherein said sample is blood, plasma, serum, cerebrospinal fluid, brain tissue, cornea tissue, urine, fecal matter, soil, bone meal, beef, beef by-products, sheep, sheep by-products, deer, deer by-products, elk, elk by-products, water or milk.

7. A method of isolating prion protein in a sample comprising contacting said sample with streptavidin under conditions permitting streptavidin to bind to prion protein and isolating prion protein bound to streptavidin.

8. The method of claim 7 wherein the prion protein is $PrP^c$ protein, $PrP^{sc}$ protein, or a variant thereof.

9. The method of claim 7 wherein the streptavidin is bound to a detectable marker.

10. The method of claim 9 wherein the detectable marker is selected from the group consisting of a fluorescence marker, an enzyme, and a radiolabeled marker.

11. The method of claim 10 wherein the detectable marker is an enzyme, and the enzyme is phosphatase.

12. The method of claim 7 wherein streptavidin is bound to a solid support.

* * * * *

SEQUENCE LISTING

```
<160> NUMBER OF SEQ ID NOS: 6

<210> SEQ ID NO 1
<211> LENGTH: 8
<212> TYPE: PRT
<213> ORGANISM: homo sapiens

<400> SEQUENCE: 1

Gly Tyr Gly Gln Pro His Gly Gly
1               5

<210> SEQ ID NO 2
<211> LENGTH: 8
<212> TYPE: PRT
<213> ORGANISM: artificial sequence
<220> FEATURE:
<221> NAME/KEY: peptide
<222> LOCATION: (1)..(8)
<223> OTHER INFORMATION: peptide synthesized directly onto resin;
      used in binding assay

<400> SEQUENCE: 2

Gly His Gly Gln Gly Pro Gly Tyr
1               5

<210> SEQ ID NO 3
<211> LENGTH: 6
<212> TYPE: PRT
<213> ORGANISM: artificial sequence
<220> FEATURE:
<221> NAME/KEY: peptide
<222> LOCATION: (1)..(6)
<223> OTHER INFORMATION: peptide sequence synthesized directly onto
      resin; used in binding assay

<400> SEQUENCE: 3

Thr Pro His Pro Gln Gly
1               5

<210> SEQ ID NO 4
<211> LENGTH: 4
<212> TYPE: PRT
<213> ORGANISM: homo sapiens

<400> SEQUENCE: 4

Met Lys His Met
1

<210> SEQ ID NO 5
<211> LENGTH: 7
<212> TYPE: PRT
<213> ORGANISM: artificial sequence
<220> FEATURE:
<221> NAME/KEY: peptide
<222> LOCATION: (1)..(7)
<223> OTHER INFORMATION: peptide sequence that interacts with
      streptavidin

<400> SEQUENCE: 5

Phe Ser His Pro Gln Asn Thr
1               5

<210> SEQ ID NO 6
<211> LENGTH: 7
<212> TYPE: PRT
<213> ORGANISM: artificial sequence
```

-continued

```
<220> FEATURE:
<221> NAME/KEY: peptide
<222> LOCATION: (1)..(7)
<223> OTHER INFORMATION: peptide sequence that interacts with
      streptavidin

<400> SEQUENCE: 6

His Asp His Pro Gln Asn Leu
1               5
```